(12) United States Patent
McDaniel

(10) Patent No.: US 7,976,525 B2
(45) Date of Patent: Jul. 12, 2011

(54) COMPOUND ABSORBENT ARTICLE WITH IMPROVED BODY CONTACT

(75) Inventor: Mary Lou McDaniel, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 398 days.

(21) Appl. No.: 12/215,535

(22) Filed: Jun. 27, 2008

(65) Prior Publication Data

US 2009/0204095 A1    Aug. 13, 2009

Related U.S. Application Data

(60) Provisional application No. 61/065,801, filed on Feb. 13, 2008.

(51) Int. Cl.
*A61F 13/15*    (2006.01)
(52) U.S. Cl. ........ 604/393; 604/397; 604/398; 604/402
(58) Field of Classification Search .................. 604/393, 604/397, 398, 402
See application file for complete search history.

(56) References Cited

U.S. PATENT DOCUMENTS

| | | |
|---|---|---|
| 3,183,909 A | 5/1965 | Roehr |
| 3,654,929 A | 4/1972 | Nilsson et al. |
| 4,372,312 A | 2/1983 | Fendler et al. |
| 4,425,130 A | 1/1984 | Desmarais |
| 4,605,405 A | 8/1986 | Lassen |
| 4,631,062 A | 12/1986 | Lassen et al. |
| 4,908,026 A | 3/1990 | Sukiennik et al. |
| 4,917,697 A | 4/1990 | Osborn, III et al. |
| 5,007,906 A | 4/1991 | Osborn, III et al. |
| 5,324,278 A | 6/1994 | Visscher et al. |
| 5,507,735 A | 4/1996 | Van Iten et al. |
| 5,591,148 A | 1/1997 | McFall et al. |
| 5,611,790 A | 3/1997 | Osborn, III et al. |
| 5,662,639 A | 9/1997 | Tanaka et al. |
| 5,674,214 A | 10/1997 | Visscher et al. |
| 5,695,324 A | 12/1997 | Weirich |
| 5,795,349 A | 8/1998 | Lavash et al. |
| 5,810,798 A | 9/1998 | Finch et al. |
| 5,827,258 A | 10/1998 | McFall et al. |
| 5,833,680 A | 11/1998 | Hartman |
| 5,853,401 A | 12/1998 | Mayer et al. |
| 5,885,268 A | 3/1999 | Bien et al. |
| 5,961,508 A | 10/1999 | Mayer et al. |
| 5,972,806 A | 10/1999 | Weinberger et al. |
| 6,114,597 A | 9/2000 | Romare |
| 6,183,456 B1 * | 2/2001 | Brown et al. ............ 604/385.01 |
| 6,241,714 B1 | 6/2001 | Raidel et al. |
| 6,348,047 B1 | 2/2002 | Harper |
| 6,358,234 B1 | 3/2002 | Terada et al. |
| 6,387,084 B1 | 5/2002 | VanGompel et al. |
| 6,416,501 B2 | 7/2002 | Brown et al. |

(Continued)

FOREIGN PATENT DOCUMENTS

EP    0 067 465 B 1    9/1986

(Continued)

*Primary Examiner* — Jacqueline F Stephens
(74) *Attorney, Agent, or Firm* — Denise L. Stoker; David J. Arteman

(57) ABSTRACT

A personal care absorbent article has compound construction, a pad connected to an anchor. In use, the anchor is associated with a wearer's undergarment. The pad is attached to the anchor by a tether system, which allows the pad to at least partially decouple from the anchor.

13 Claims, 10 Drawing Sheets

U.S. PATENT DOCUMENTS

| | | |
|---|---|---|
| 6,423,043 B1 | 7/2002 | Gustafsson |
| 6,677,498 B2 | 1/2004 | Chen et al. |
| 6,695,827 B2 | 2/2004 | Chen et al. |
| 6,902,552 B2 | 6/2005 | VanGompel et al. |
| 6,984,225 B2 | 1/2006 | Raidel et al. |
| 7,063,689 B2 | 6/2006 | VanGompel et al. |
| 7,145,054 B2 | 12/2006 | Zander et al. |
| 7,566,330 B2 | 7/2009 | Sugiyama et al. |
| 2001/0021834 A1 | 9/2001 | Yoshimasa |
| 2004/0181201 A1 | 9/2004 | Mizutani et al. |
| 2004/0186448 A1 | 9/2004 | Misek et al. |
| 2005/0004546 A1 | 1/2005 | Mizutani et al. |
| 2005/0004547 A1 | 1/2005 | Lavash |
| 2005/0010185 A1 | 1/2005 | Mizutani et al. |
| 2005/0027277 A1 | 2/2005 | Mizutani et al. |
| 2005/0124953 A1 | 6/2005 | Woltman et al. |
| 2005/0137553 A1 | 6/2005 | Bechyne et al. |
| 2005/0187531 A1 | 8/2005 | Alcantara et al. |
| 2005/0234418 A1 | 10/2005 | Yoshimasa et al. |
| 2007/0287973 A1 | 12/2007 | Cohen et al. |
| 2009/0036858 A1 | 2/2009 | Van Den Bogart et al. |

FOREIGN PATENT DOCUMENTS

| | | |
|---|---|---|
| EP | 0 162 451 B1 | 8/1991 |
| EP | 0 345 703 B1 | 9/1992 |
| EP | 0 335 527 B1 | 11/1992 |
| EP | 0 335 253 B1 | 3/1993 |
| EP | 0 304 644 B1 | 10/1993 |
| EP | 0 496 709 B1 | 10/1996 |
| EP | 0 425 026 B1 | 12/1996 |
| EP | 0 543 116 B1 | 6/1997 |
| EP | 0 599 380 B1 | 10/1997 |
| EP | 1 048 277 A2 | 11/2000 |
| EP | 0 335 252 B1 | 12/2001 |
| EP | 0 956 843 B1 | 1/2003 |
| EP | 1 040 798 B1 | 3/2003 |
| EP | 1 293 186 A2 | 3/2003 |
| EP | 0 880 955 B1 | 7/2003 |
| EP | 1 142 546 B1 | 12/2005 |
| EP | 1 637 106 A2 | 3/2006 |
| EP | 1 637 108 A2 | 3/2006 |
| EP | 1 097 686 B1 | 4/2006 |
| EP | 1 097 685 B1 | 5/2006 |
| EP | 1 269 953 B1 | 9/2006 |
| EP | 1 707 171 A2 | 10/2006 |
| EP | 1 188 425 B1 | 12/2006 |
| EP | 1 779 828 A1 | 5/2007 |
| JP | 2007-130446 | 5/2007 |
| JP | 2007-167191 | 7/2007 |
| WO | WO 91/16873 A1 | 11/1991 |
| WO | WO 92/07535 A1 | 5/1992 |
| WO | WO 93/06805 A1 | 4/1993 |
| WO | WO 95/16424 A1 | 6/1995 |
| WO | WO 95/28137 A2 | 10/1995 |
| WO | WO 96/00546 A1 | 1/1996 |
| WO | WO 96/05790 A1 | 2/1996 |
| WO | WO 96/20668 A1 | 7/1996 |
| WO | WO 96/41602 A1 | 12/1996 |
| WO | WO 97/09014 A1 | 3/1997 |
| WO | WO 97/14389 A1 | 4/1997 |
| WO | WO 97/28773 A1 | 8/1997 |
| WO | WO 98/20823 A2 | 5/1998 |
| WO | WO 98/27909 A1 | 7/1998 |
| WO | WO 98/58613 A1 | 12/1998 |
| WO | WO 98/58614 A1 | 12/1998 |
| WO | WO 99/03436 A1 | 1/1999 |
| WO | WO 99/15123 A1 | 4/1999 |
| WO | WO 99/16397 A1 | 4/1999 |
| WO | WO 99/23984 A1 | 5/1999 |
| WO | WO 00/00235 A1 | 1/2000 |
| WO | WO 00/13633 A1 | 3/2000 |
| WO | WO 00/21477 A1 | 4/2000 |
| WO | WO 00/25712 A1 | 5/2000 |
| WO | WO 00/25713 A1 | 5/2000 |
| WO | WO 00/37001 A1 | 6/2000 |
| WO | WO 00/37002 A1 | 6/2000 |
| WO | WO 00/40198 A2 | 7/2000 |
| WO | WO 01/45622 A1 | 6/2001 |
| WO | WO 2004/073569 A1 | 9/2004 |
| WO | WO 2004/073570 A1 | 9/2004 |
| WO | WO 2004/073571 A1 | 9/2004 |
| WO | WO 2005/000176 A2 | 1/2005 |
| WO | WO 2005/046990 A2 | 5/2005 |
| WO | WO 2007/144791 A1 | 12/2007 |

* cited by examiner

COMPOUND ABSORBENT ARTICLE WITH IMPROVED BODY CONTACT

This application claims the benefit under 35 U.S.C. 119(e) to provisional application Ser. No. 61/065,801 filed in the U.S. Patent and Trademark Office on Feb. 13, 2008. The entirety of provisional application Ser. No. 61/065,801 is hereby incorporated by reference.

BACKGROUND OF THE INVENTION

The invention disclosed herein relates to disposable absorbent articles, particularly pads for absorbing menses or urine, and more particularly pads for providing improved contact with the perineal region of the body.

Absorbent articles such as sanitary napkins, panty liners, and incontinence pads are designed to absorb and retain fluid discharges from the human body. It is desirable that such absorbent articles, maintain contact with the body of the wearer when they are worn. It is even more desirable that absorbent articles conform as closely as possible to the body contours of the wearer. A body-conforming characteristic can increase the effectiveness of the absorbent article by reducing the possibility that fluids such as menses or urine will leak past the perimeter of the absorbent article.

Under dynamic conditions, such as during the normal movement by the wearer, maintaining an absorbent garment such as a sanitary napkin against the body of the wearer is difficult because there are forces which reduce the absorbent garment's ability to stay in contact with the body of the wearer. First, there are the forces associated with attachment of the absorbent garment to the wearer's clothes. Second, there are the forces associated with body movement, in particular, thigh movement.

Absorbent articles such as sanitary napkins are typically fastened to the wearer's undergarment by a pressure sensitive adhesive or other means. The means is stressed when the wearer moves about because the wearer's undergarments may not move in concert with the body of the wearer. Likely, the absorbent article will pull away from the body or may become detached from the undergarment. This can cause the sanitary napkin to shift from the desired position and registration with the wearer's vaginal opening.

As soon as the sanitary napkin is put on, for instance, the sanitary napkin is subjected to lateral compression by the upper portions of the wearer's thighs. The forces applied by the wearer's thighs generally tend to distort the shape of the sanitary napkin, reducing the material surface available for absorbing bodily fluid.

Movement of the product with respect to the wearer's body during use is especially unsuitable and undesirable in connection with those products which have been given a special shape in order to better conform the anatomy of the wearer, or in which the absorption capacity has been optimized with the requirement that the main part of the body fluid which is to be absorbed impinges on the product within a limited predetermined region of the product.

It is, therefore, desirable to provide body-conforming, fluid-absorbing, absorbent articles with a mechanism to accommodate the independence of movement between the body of the wearer and the wearer's undergarments.

SUMMARY OF THE INVENTION

One aspect of the present invention is a method of maintaining contact between an absorbent pad having a bodyfacing surface, and a perineal-region orifice of the human body. The method includes the steps of: (a) connecting an absorbent pad to an anchor member by at least two connectors that allow at least a portion of the absorbent pad to move in a longitudinal, lateral, and vertical direction with respect to the anchor member; (b) providing instructions to align the pad with the perineal region orifice and (c) folding the absorbent pad along a longitudinal axis so that the body-facing surface faces outward, and maintaining the folded configuration in a package prior to use.

BRIEF DESCRIPTION OF THE DRAWINGS

While the specification concludes with claims particularly pointing out and distinctly claiming the presenting invention, it is believed the same will be better understood from the following description taken in conjunction with the accompanying drawings wherein like parts are given the same reference numeral, and similar or analogous parts are designated with an additional alpha character, and:

DEFINITIONS

Figure 1:
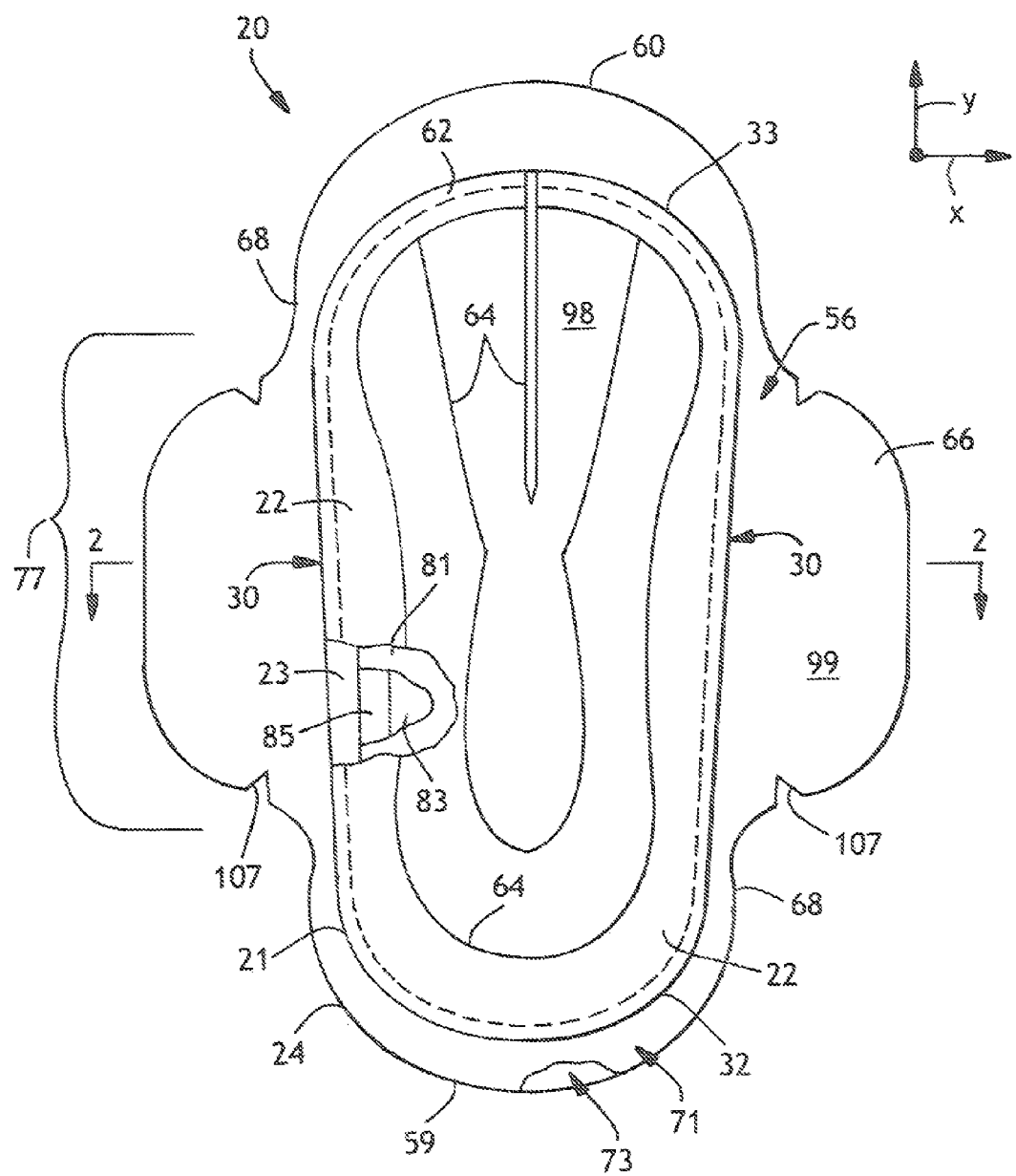
FIG. 1 is a top plan view, partially shown in cutaway, of an absorbent article according to the present invention.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

By the term "normal movement by the wearer" it is meant any movement that normally occurs during use of the absorbent article, including, walking, running, sitting, standing, kneeling, riding a bicycle, exercising, playing sports, getting into and out of an automobile, and other similar movements made by users when wearing an absorbent article.

As used herein, the term "decoupled" refers to the independence of movement of the absorbent pad 21 and the anchor 24, and requires at least the possibility of complete separation of these components while maintaining attachment to a tether system 70. The complete separability of the two components allows pad 21 to move in the longitudinal, vertical, and/or horizontal directions with respect to the anchor 24 in addition to a pivotal direction.

As used herein, the term "partially decoupled" refers to the independence of movement of the absorbent pad 21 and the anchor 24, and requires at least the possibility of complete separation of these components completely surrounding a select location of attachment.

As used herein, the term "joined" refers to the condition where a first member or component is attached, or connected, to a second member or component either directly; or indirectly, where the first member or component is attached, or connected, to an intermediate member or component which in turn is attached, or connected, to the second member or component. The relationship between the first and second joined members or components is intended to remain for the life of the members or components.

As used herein, the term "unattached" refers to the condition where two members or components are not joined.

As used herein, the term "affixed" refers to a temporary contacting relationship between two members or components of the absorbent article 20.

As used herein, the term "associated" comprises integral, joined, affixed, indirect, and weakly linked relationships.

As used herein, the term "longitudinal" refers to a line, axis or direction generally aligned with the vertical plane which bisects the standing wearer into left and right body halves.

The term "transverse" refers to the line, axis or direction generally orthogonal the longitudinal direction and lying within the plane of the absorbent article 20. The absorbent article 20 is typically longer in the longitudinal dimension than in the transverse dimension. If a side edge or transverse end is curved, a line taken at the apex of the curve will be used to determine the direction. Side edges may be oriented generally in a longitudinal direction, yet converge toward each other at either of the transverse ends.

The absorbent article 20 according to the present invention is a pad that can decouple from an anchor member in the Z-direction. As used herein, the "Z-direction" is the direction which is orthogonal the plane of the absorbent article when it is in the flat, laid out condition of FIG. 1. The axis of the Z-direction is generally oriented towards the wearer while the absorbent article is worn. The X-Y plane is orthogonal the Z-direction axis, encompasses the longitudinal and transverse axes, and is coincident with the plane of the inwardly oriented surface of the backsheet 50 when the absorbent article is in the flat, laid-out condition of FIG. 1.

As used herein, the term "polymer" generally includes, but is not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to, isotactic, syndiotactic and random symmetries.

As used herein, "body-facing surface" means a surface of the absorbent article which is intended to be disposed toward or placed adjacent to the body of the wearer during ordinary use. The "garment-facing surface" is on the opposite side of the absorbent article from the body-facing surface. The garment-facing surface is an outward surface of the absorbent article and is intended to be disposed to face away from the wearer's body during ordinary use. The garment-facing surface is generally arranged to face toward or placed adjacent to the wearer's undergarments when the absorbent article is worn.

As used herein, "flaccid" refers to a slackened state in the Z-direction.

The absorbent pad 21 of the absorbent article 20 may be divided longitudinally in 3 portions that are equal in length. The portion coinciding with the nose end is the anterior portion. The portion coinciding with the tail end is the posterior portion. The middle portion is located between the anterior and posterior portions. Similarly, the absorbent pad 21 may be divided laterally into zones, namely a first and second side zone, and a middle zone. The zones and portions are described in more detail herein.

DETAILED DESCRIPTION OF THE INVENTION

In its various arrangements, absorbent article 20 can be configured to provide a personal care absorbent product, such as an infant diaper, an adult incontinence product or the like. In desired configurations, the article 20 can provide a feminine hygiene product (e.g., a sanitary napkin, a panty liner, an interlabial device, or the like).

Figure 2:
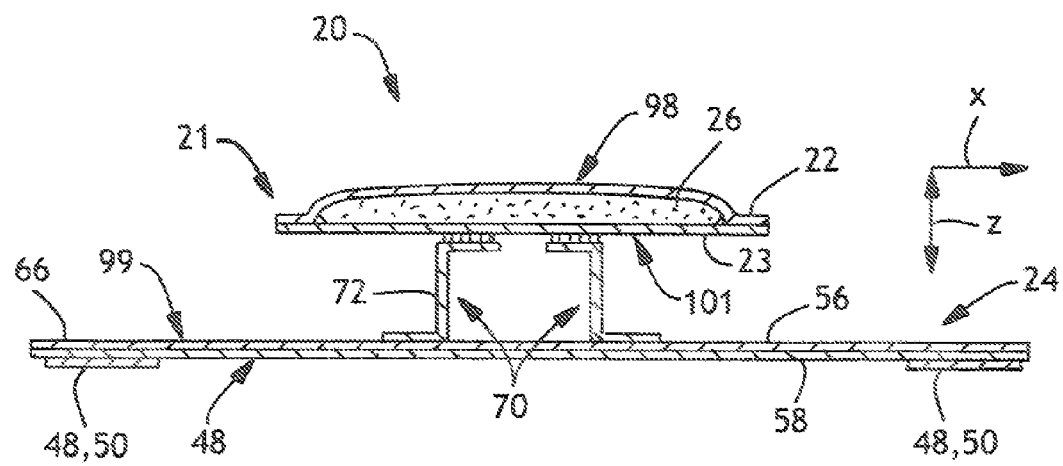
FIG. 2 is a vertical sectional view taken along lines 2-2 of FIG. 1, showing the absorbent article articulated to an open and decoupled position.
Figure 2A:
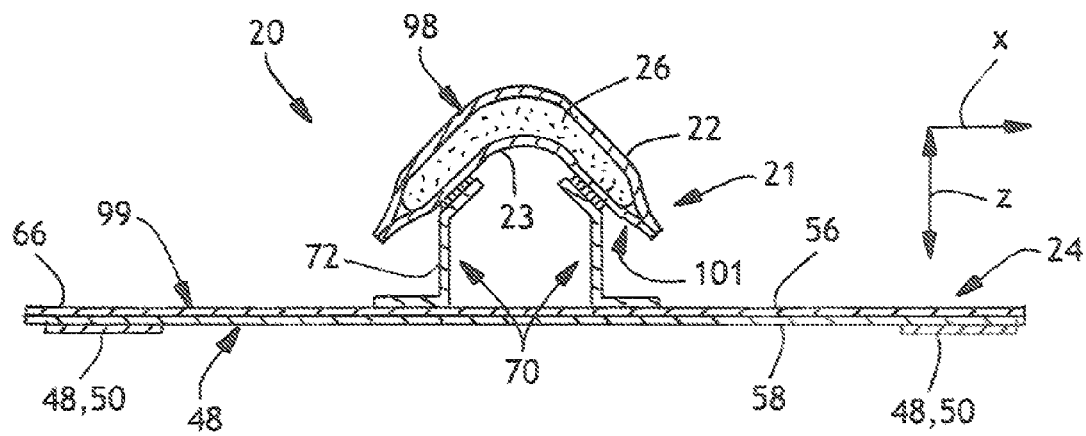
FIG. 2A is the vertical section shown in FIG. 2, showing how the absorbent pad may be pre-formed to have a peaked profile.

As illustrated in FIGS. 1-2A, a first embodiment of an absorbent article 20 according to the present invention is in the form of a sanitary napkin or pad. The absorbent article 20 includes an absorbent pad 21 constructed from a liquid-permeable topsheet 22 which is oriented towards and contacts the body of a wearer, a backsheet 23 which is oriented away from the wearer's body, and an absorbent body 26 located therebetween. A liquid-impermeable anchor 24, which is intended to be oriented towards and contact the undergarment of the wearer, is joined to the absorbent pad 21 by a tether system 70. The tether system 70 allows pad 21 to be partially or fully decoupled from the anchor 24 in not only a vertical z-direction, but also in the x- and y-direction.

The article 20 can have a lengthwise, longitudinal direction that extends along an appointed y-axis of the article, and a lateral cross-direction which can extend along an appointed x-axis of the article. For ease of illustration, the pad 21 is illustrated in FIGS. 1 and 2 as being flattened. However, in a desired embodiment, the pad 21 may be preformed so that it has a fold along the longitudinal y-axis. The resulting profile is a peaked profile, as shown in FIG. 2A.

The absorbent pad 21 is defined by two side edges 30 and two ends, namely nose end 32 and tail end 33. However, examining the pad 21 can have any desired shape. For example, the pad 21 may have a dog bone shape, an oval shape, an egg shape, a racetrack shape, an hourglass shape, or any other desirable shape. Additionally, the pad 21 may be longitudinally symmetric or asymmetric, as desired. In the exemplary pad of FIG. 1, side edges 30 are very generally oriented in the longitudinal direction, whereas the nose end 32 and the tail end 33 are separated longitudinally and are very generally oriented in the lateral direction.

Pad topsheet 22 is a component of the absorbent pad 21 which is oriented towards and contacts the body of the wearer to receive bodily discharges. The topsheet 22 is liquid permeable, and may be constructed from any operative material. For example, the topsheet can include a woven fabric, a nonwoven fabric, a polymer film, a film-fabric laminate or the like, as well as combinations thereof. Examples of a nonwoven fabric include spunbond fabric, meltblown fabric, coform fabric, a carded web, a bonded-carded-web, a bicomponent spunbond fabric or the like as well as combinations thereof. Other examples of suitable materials for constructing the cover layer can include rayon, bonded carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof. In desired arrangements, the topsheet can be configured to be operatively liquid-permeable.

A more particular example of a suitable topsheet 22 material can include a bonded-carded-web composed of polypropylene and polyethylene, such as has been used as a cover stock for KOTEX brand pantiliners, and has been obtainable from Vliesstoffwerk Christian Heinrich Sandler GmbH & Co. KG, a business having an address at Posffach 1144, D95120 Schwarzenbach/Saale, Germany. Other examples of suitable materials are composite materials of a polymer film and a nonwoven fabric material. The composite materials are typically in the form of integral sheets generally formed by laminating the polymer film with a web of spunbond material. The process to combine these two materials is well described in the art.

In a desired arrangement, the topsheet 22 can be configured to be operatively liquid-permeable with regard to the liquids that the article is intended to absorb or otherwise handle. The operative liquid-permeability may, for example, be provided by a plurality of pores, perforations, apertures or other openings, as well as combinations thereof, that are present or formed in the cover layer. The apertures or other openings can help increase the rate at which bodily liquids can move through the thickness of the cover layer and penetrate into the other components of the article (e.g. into the absorbent body 26). The selected arrangement of liquid-permeability is desirably present at least on an operative portion of the cover layer that is appointed for placement on the body-side surface 98 of the pad 21.

The topsheet 22 can provide comfort and conformability, and can function to direct bodily exudates away from the body and toward the absorbent body 26. In a desired feature, the topsheet 22 can be configured to retain little or no liquid in its structure, and can be configured to provide a relatively comfortable and non-irritating surface next to the body-tissues of a female wearer.

The topsheet 22 may have at least a portion of its bodyside surface 98 treated with a surfactant and/or a menses modifier to increase the surface energy of the material surface or reduce the viscoelastic properties of the menses, and to render the cover more hydrophilic and more wettable to body fluids.

The surfactant can permit arriving bodily liquids to more readily penetrate the cover layer. The surfactant may also diminish the likelihood that the arriving bodily fluids, such as menstrual fluid, will flow off the cover layer rather than penetrate through the cover layer into other components of the article (e.g. into the absorbent body structure). In a particular configuration, the surfactant can be substantially evenly distributed across at least a portion of the upper, bodyside surface 98 of the topsheet 22 that overlays the upper, bodyside surface of the absorbent body 26. In another embodiment of the present invention, the topsheet 22 may be treated with a lotion or fragrance.

The topsheet 22 may be maintained in secured relation with the absorbent body 26 by bonding all or a portion of the adjacent surfaces to one another. A variety of bonding articles known to one of skill in the art may be utilized to achieve any such secured relation. Examples of such articles include, but are not limited to, the application of construction adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent. The topsheet 22 typically extends over the upper, bodyside surface of the absorbent structure, but can alternatively extend around the article to partially or entirely surround or enclose the absorbent body and backsheet 23.

The backsheet 23 is the first constraint for bodily discharges which migrate towards the anchor 24. The backsheet 23 may include a layer constructed of any material that can function as a constraint for bodily discharges, and may have a selected level of liquid-permeability or liquid-impermeability, as desired.

In one particular embodiment of the present invention, backsheet 23 may be configured to provide an operatively liquid-impermeable barrier. The backsheet may, for example, include a polymeric film, a woven fabric, a nonwoven fabric or the like, as well as combinations or composites thereof. For example, the backsheet may include a polymer film laminated to a woven or nonwoven fabric. In a particular feature, the polymer film can be composed of polyethylene, polypropylene, polyester or the like, as well as combinations thereof.

Desirably, the backsheet 23 can operatively permit a sufficient passage of air and moisture vapor out of the article, particularly out of an absorbent (e.g. storage or absorbent structure 30) while blocking the passage of bodily liquids. An example of a suitable backsheet material can include a breathable, microporous film, such as a HANJIN Breathable Backsheet available from Hanjin Printing, Hanjin P&C Company Limited, a business having offices located in Sahvon-Ii.Jungan-mvu.Kongiu-City, Chung cheong nam-do, Republic of South Korea. This exemplary backsheet material is a breathable film, which is dimple embossed and contains: 47.78% calcium carbonate, 2.22% TiO2, and 50% polyethylene.

The backsheet 23 may be adhesively joined to the absorbent body 26 with a construction adhesive, two-sided surgical tape, or the like. Suitable construction adhesive such as NS-5610 can be obtained from National Starch LLC, Somerville, N.J. The backsheet 23 may be joined to the absorbent body 26 throughout the entire surface area of the backsheet 23, but this arrangement could result in an absorbent article 20 of lower flexibility. The backsheet 23 is preferably peripherally joined to the underside surface of the absorbent body 26 which is oriented towards the anchor 24.

In a particular feature, the polymer film of backsheet 23 may have a minimum thickness of no less than about 0.025 mm, and in another feature, the polymer film can have a maximum thickness of no greater than about 0.13 mm. Bicomponent films or other multi-component films can also be used, as well as woven and/or nonwoven fabrics which have been treated to render them operatively liquid-impermeable. Another suitable backsheet material can include closed cell polyolefin foam. For example, closed cell polyethylene foam may be employed. Still another example of a backsheet material would be a material that is similar to a polyethylene film which is used on commercially sold KOTEX brand pantiliners, and is obtainable from Pliant Corporation, a business having offices located in Schaumburg, Ill., USA.

Referring to FIG. 2, the structure of the absorbent body 26 can be operatively configured to provide desired levels of liquid retention and storage capacity, and desired levels of liquid acquisition and distribution. More particularly, the absorbent body can be configured to hold a liquid, such as urine, menses, other complex liquid or the like, as well as combinations thereof.

As representatively shown, the absorbent body 26 may be a single layer of absorbent materials or may be a multilayer structure. Each of the layers can contain similar materials or different materials. In the absorbent article 20 of the present invention, the materials which may be used to form the absorbent body 26 include those materials conventionally used in absorbent articles and includes materials, such as, for example, cellulose, wood pulp fluff, rayon, cotton, and meltblown polymers such as polyester, polypropylene or coform. Coform is a meltblown air-formed combination of meltblown polymers, such as polypropylene, and absorbent staple fibers, such as cellulose. A desired material is wood pulp fluff, for it is low in cost, relatively easy to form, and has good absorbency. It is possible to include a superabsorbent material, as described herein.

The absorbent body 26 can also be formed from a composite made of a hydrophilic material which may include various natural or synthetic fibers, wood pulp fibers, regenerated cellulose or cotton fibers, or a blend of pulp and other fibers. One particular example of a material which may be used as the absorbent body 26 is an airlaid material. The absorbent body 26 may have other properties including extensibility, which may allow the absorbent body to be extended or fit to a particular user. One example of extensible absorbent bodies is described in U.S. Pat. No. 5,611,790, issued Mar. 18, 1997, to Osborn, III et al., herein incorporated by reference in its entirety.

In one desired embodiment of the present invention, the absorbent body 26 includes a surge layer, a meltblown layer, and an absorbent layer. Many absorbent body configurations may be used, such as the examples described below, or the absorbent bodies described in U.S. patent Ser. No. 10/392, 116, filed by Berceau et al. on May 19, 2003; and U.S. patent Ser. No. 11/890,093, filed by VanDenBogart et al. on Aug. 3, 2007; both incorporated herein to the extent that they are not in conflict with the present invention.

Desirably, the surge layer is the layer immediately underneath and in contact with the topsheet 22. The surge layer 81, sometimes referred to as an intake layer, may be sized and placed to more effectively operate in a target area of the absorbent body 26 where liquids are more likely to be introduced into the pad 21. The surge layer can include material that is configured to quickly absorb and pull liquid away from the body. Accordingly, the surge layer 81 may provide the function of liquid intake and can also provide the functions of liquid distribution, spreading, temporary storage and liquid retention. The surge layer may include natural fibers, synthetic fibers, a woven fabric, a nonwoven fabric, a wet-laid fibrous web, a coform web, a substantially unbonded air-laid fibrous web, an operatively bonded stabilized-airlaid fibrous web, or the like, as well as combinations thereof.

In a particular arrangement, the surge layer can be a thermally-bonded, stabilized airlaid fibrous web (e.g. Concert code 175.1020) available from Concert Fabrication, a business having offices located in Gatineaux, Quebec, Canada. The surge layer may optionally be provided by a similar, stabilized airlaid fibrous web available from Buckeye Technologies, Inc., a business having offices located in Memphis, Tenn., U.S.A.

Figure 12:
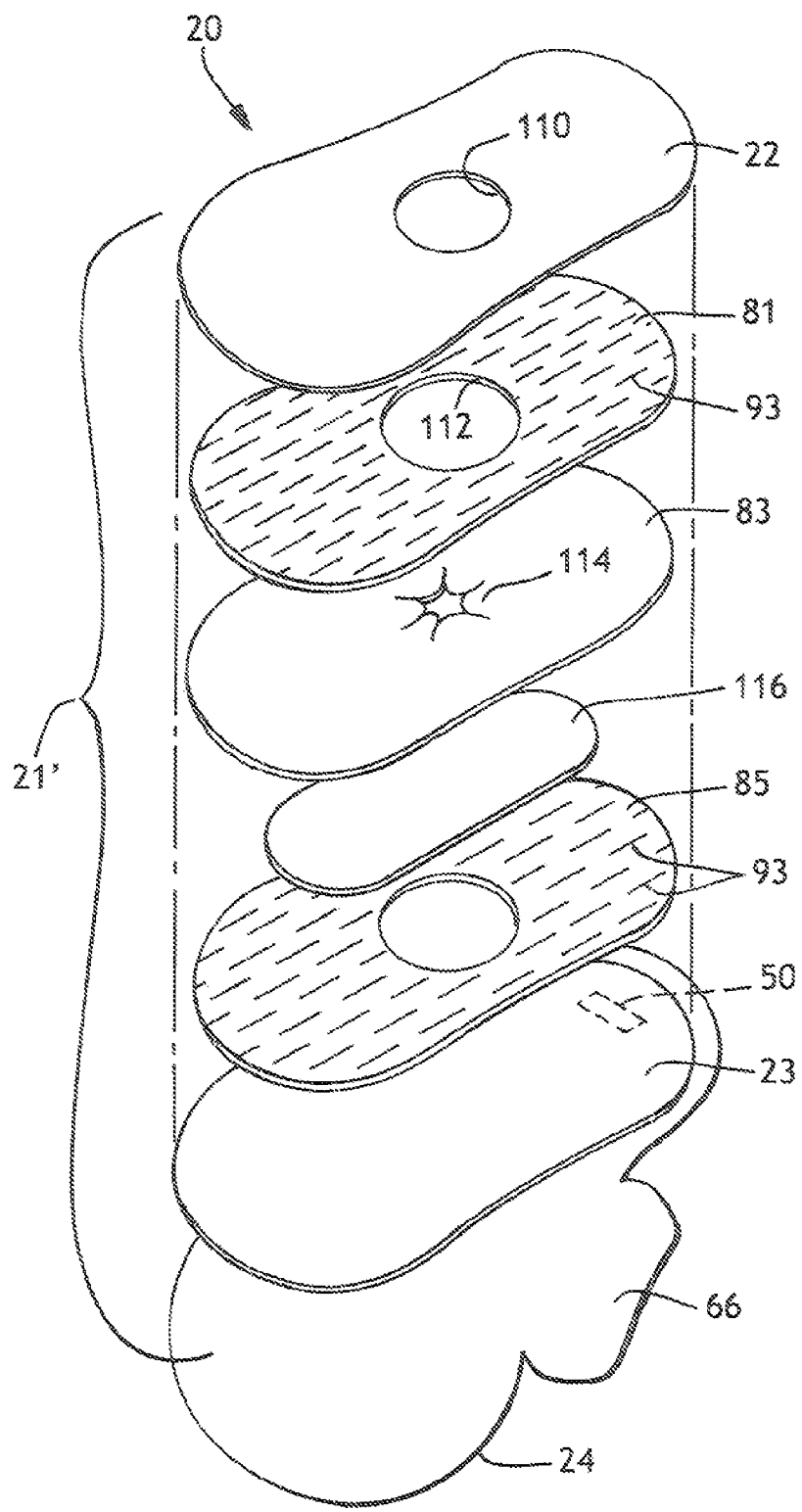
FIG. 12 is an exploded view of the article shown in FIG. 11.

In a most desired embodiment, the surge layer 81 is slitted or scored at a body-facing surface so that it can more easily conform to the body of the user. For example, see one possible array of slits 93 of FIG. 12 (note that FIG. 12 is a different embodiment than that of FIG. 1).

In one embodiment, directly underneath and in contact with the surge layer is the meltblown layer 83. The optional meltblown layer 83 is configured to provide a layer that is denser than the surge layer 81 and the absorbent shaping layer 85. Each such layer has a footprint or area defined by a body-side surface or garment-side surface, both equal in area. In particular aspects, the meltblown layer 83 area can be at least a minimum of about 1.25 times a surge-layer area (1.25×). The shaping layer 85 area can alternatively be at least about 1.5 times the surge layer area, and can optionally be at least about 1.75 times the surge layer area to provide improved performance.

Directly underneath the meltblown layer is the absorbent layer or "shaping" layer. The absorbent layer or shaping layer 85 can provide the functions of liquid storage and retention, liquid distribution, liquid spreading and shape maintenance. The shaping layer 85 may include natural fibers, synthetic fibers, superabsorbent materials (described herein), a woven fabric; a nonwoven fabric; a wet-laid fibrous web; a substantially unbonded airlaid fibrous web; an operatively bonded, stabilized-airlaid fibrous web; or the like, as well as combinations thereof. Additionally, the shaping layer 85 may include one or more components that can modify the menses or intramenstrual liquid.

In other aspects, the shaping layer area can be up to a maximum of about 5 times the surge layer area, or more. The shaping layer 85 area can alternatively be up to about 4 times the surge layer area, and can optionally be up to about 3.3 times the surge layer area to provide improved effectiveness. In a desired arrangement the intake-layer can be about 2.5 times the surge layer area.

In a particular arrangement, the shaping layer 85 can be a thermally-bonded, stabilized airlaid fibrous web available from Concert Fabrication (Concert code 225.1021), a business having offices located in Gatineaux, Quebec, Canada (e.g. Concert code 225.1021). The shaping layer 85 may optionally be provided by a similar, stabilized airlaid fibrous web available from Buckeye Technologies, Inc., a business having offices located in Memphis, Tenn., U.S.A.

In a most desired embodiment, the shaping layer 85 is slitted or scored at a body-facing surface so that it can more easily conform the body of the user. For example, see one possible array of slits 93 of FIG. 12 (note that FIG. 12 is a different embodiment than that of FIG. 1).

The shaping layer 85 can have a higher basis weight, as compared to the surge layer 81, but may optionally have a similar or equal basis weight. In another feature, the density of the shaping layer 85 can be greater than that of the surge layer 81, and may include a density gradient through the material of the intake layer (e.g. with higher densities positioned relatively closer to the bottom, garment-side of the article).

In a particular embodiment of the present invention, the basis weight of the shaping layer 85 can be at least a minimum of about 100 g/m2. The shaping layer basis weight can alternatively be at least about 130 g/m2, and can optionally be at least about 165 g/m2 to provide improved performance. In other aspects, the basis weight of the shaping layer can be up to a maximum of about 400 g/m2, or more. The shaping layer basis weight can alternatively be up to about 350 g/m2, and can optionally be up to about 325 g/m2 to provide improved effectiveness. In a desired configuration, the shaping layer basis weight can be about 225 g/m2.

If the basis weight of the shaping layer 85 is outside the desired values, various disadvantages may occur. For example, an overly high basis weight of the shaping layer can provide a product that is excessively bulky and uncomfortable to the wearer during use. Additionally, the product cost may become too high. An overly low basis weight of the shaping layer can excessively increase the incidence of bunching, twisting and roping of the absorbent pad structure. As a result, the article can excessively leak and reduce consumer confidence in the product performance. Additionally, the liquid transfer from the intake layer to the shaping layer can be excessively decreased, and the absorbent capacity of the shaping layer can become too low. As a result, the article can exhibit excessive leakage and excessive wetness against the wearer's skin.

In a further embodiment of the present invention, the density of the shaping layer 85 can be at least a minimum of about 0.06 g/cm3. The shaping layer density can alternatively be at least about 0.07 g/cm3, and can optionally be at least about 0.08 g/cm3 to provide improved performance. In other aspects, the density of the shaping layer can be up to a maximum of about 0.3 g/cm3, or more. The shaping layer density can alternatively be up to about 0.2 g/cm3, and can optionally be up to about 0.16 g/cm3 to provide improved effectiveness. In a desired arrangement, the density of the shaping layer 85 can be about 0.12 g/cm3.

If the density of the shaping layer 85 is outside the desired values, various disadvantages may occur. For example, an overly high density of the shaping layer can provide an excessively stiff article which is uncomfortable during use. Additionally, depending on the basis weight and thickness of the shaping layer, the absorbent structure can exhibit excessive bunching, twisting and roping, and can cause discomfort and poor fit. An overly high density can excessively reduce the permeability and absorbent capacity of the shaping layer. As a result, the liquid transfer can be poor, and the article can prematurely leak. In a stabilized airlaid web that contains superabsorbent material, an overly high density can excessively restrict the ability of the superabsorbent material to swell and absorb liquid. This can decrease the saturation capacity and retention capacity of the web, and can lead to premature leakage. Additionally, during production of the high density web, the high compression employed to densify the web can damage the superabsorbent material and degrade its performance. This again can allow premature leakage and excessive wetness against the wearer's skin. An overly low density in the shaping layer can provide a product that is too thick, ill fitting, and uncomfortable. Also, the permeability of the shaping layer can become too high, and the shaping layer may be unable to adequately desorb the intake layer. As a result, there can be excessive rewet and flowback of liquid to the wearer's skin.

Superabsorbent materials suitable for use in the shaping layer of the absorbent body 26 are known to those skilled in the art, and may be in any operative form, such as particulate form. Generally stated, the superabsorbent material can be a water-swellable, generally water-insoluble, hydrogel-forming polymeric absorbent material, which is capable of absorbing at least about 20, desirably about 30, and possibly about 60 times or more its weight in physiological saline (e.g. 0.9 wt % NaCl). The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers are preferably lightly crosslinked to render the material substantially water insoluble. Crosslinking may, for example, be by irradiation or covalent, ionic, Van der Waals, or hydrogen bonding. Suitable materials are available from various commercial vendors, such as Evonik Stockhausen, Inc., Essen, Germany. The superabsorbent material may desirably be included in an appointed storage or retention portion of the absorbent system, and may optionally be employed in other components or portions of the absorbent article.

The topsheet 22 and the backsheet 23 may be peripherally sealed together to enclose the absorbent body 26 to form the absorbent pad 21, as is shown in FIG. 1. When a peripheral seal 62 is in use, the absorbent body 26 is positioned between the topsheet 22 and the backsheet 23. Referring to FIGS. 1 and 2, the topsheet 22 and the backsheet 23 can have a length and a width dimension greater than the length and width of the absorbent body 26. The topsheet 22 and backsheet 23 may have an identical footprint. The topsheet 22 and the backsheet 23 may be sealed together using any suitable means that will not leave a hard, uncomfortable residue that may be annoying to the wearer. As used herein, the term "sealed" encompasses configurations whereby the topsheet 22 is directly joined to the backsheet 23 and configurations whereby the topsheet 22 is indirectly joined to the backsheet 23 by affixing the topsheet 22 to an intermediate member (not shown), which are in turn affixed to the backsheet 23. Alternatively, the topsheet 22 can be wrapped around both the absorbent body 26 and the backsheet 23 to form a wrapped pad. The topsheet 22 and backsheet 23, and other components of the absorbent product, can be joined, for example, with adhesive bonds, sonic bonds, thermal bonds, pinning, stitching or any other attachment technique known in the art, as well as combinations thereof.

Pad 21 may include any desired pattern of embossments 64 formed into at least the bodyside surface 98. The embossing can advantageously deform the bodyside of the topsheet 22 and can advantageously deform selected portions of the absorbent body 26 to provide operative channel regions that can help block, direct or otherwise control a desired movement of liquids along the bodyside surface of the article. The embossing can also provide an aesthetic benefit to the consumer, and a visual cue regarding fit and leakage protection. For example, embossments 64 can be positioned generally adjacent the perimeter edges of the absorbent body 26 such as in the tail region as shown. In other aspects, the embossments can be configured to provide a regular or irregular pattern having one or more channels which are distributed in a symmetrical or asymmetrical array, as desired.

Figure 3:
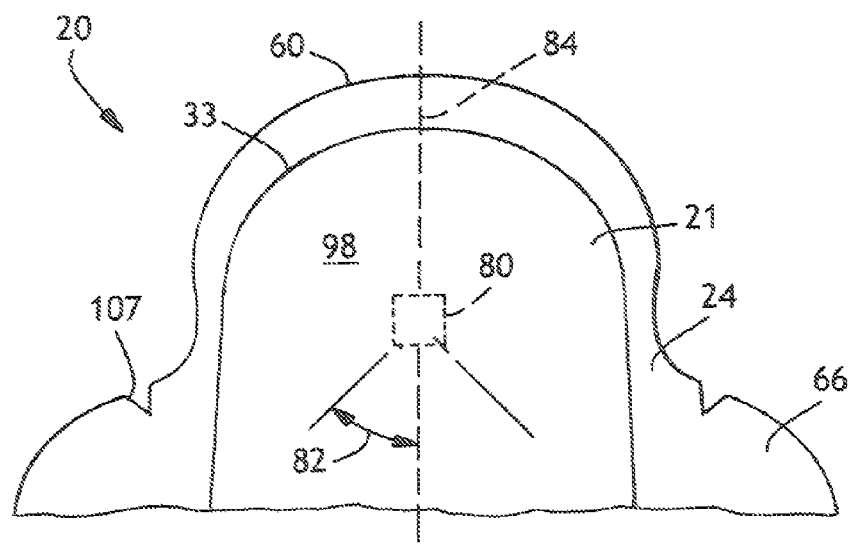
FIG. 3 is a partial plan view of the absorbent article shown in FIG. 1, demonstrating a pivotal connection between the pad and the anchor components.

Referring still to FIGS. 1 and 3, the anchor 24 serves to affix the pad 21 to an undergarment, particularly to the crotch region of the undergarment. Further, anchor 24 serves to keep undergarments clean should bodily fluids flow over the edges of the pad 21. Moreover, anchor 24 may serve as a fluid barrier, and may vary in degrees of absorbency.

Desirably, anchor 24 is flexible and relatively thin, having a thickness less than that of the pad 21. A suitable anchor 24 may be made from the low density polyethylene material, described above, used for the backsheet 23. Desirably, anchor 24 has a multilayer construction as described below.

In one embodiment of the present invention, anchor 24 will include two layers of material, a body-facing layer 71 and a garment-facing layer 73. Desirably, the body-facing layer extends to the edges of the anchor. The body-side layer may be constructed of any operative material, and may be a composite material. For example, the body-side layer 71 may include a woven fabric, a nonwoven fabric, a polymer film, a film-nonwoven fabric laminate or the like, as well as combinations thereof. Examples of a nonwoven fabric include, for example, an airlaid nonwoven web, a spunbond nonwoven web, a meltblown nonwoven web, a bonded-carded web, a hydroentangled nonwoven web, a spunlace web or the like, as well as combinations thereof. Other examples of suitable materials for constructing the body-side layer 71 can include rayon, bonded-carded webs of polyester, polypropylene, polyethylene, nylon, or other heat-bondable fibers, finely perforated film webs, net-like materials, and the like, as well as combinations thereof. These webs can be prepared from polymeric materials such as, for example, polyolefins, such as polypropylene and polyethylene and copolymers thereof, polyesters in general including aliphatic esters such as polylactic acid, nylon or any other heat-bondable materials.

Other examples of suitable materials for the body-side layer are composite materials of a polymer film and a nonwoven fabric material. The composite materials are typically in the form of integral sheets of polymer film laminated to nonwoven web, such as a spunbond material. In a particular arrangement, the body-side layer 71 can be configured to be operatively liquid-permeable with regard to the liquids that the anchor 24 is intended to absorb. The operative liquid-permeability may, for example, be provided by a plurality of pores, perforations, apertures or other openings, as well as combinations thereof, which are present or formed in the liner or body contacting layer. The apertures or other openings can help increase the rate at which bodily liquids can move through the body contacting layer and penetrate into the other components, such as an optional absorption layer (not shown). However, in a desired embodiment, the body-side layer 71 is backed only by a garment-facing layer 73. The body-side layer 71 may be embossed, printed or otherwise imparted with a pattern as is known in the art.

The garment-facing layer 73 forms the garment-facing side of the anchor 24 when worn by a user. The garment-facing layer 73 should be selected such that it will freely move against the undergarment or clothing of a user. One way to achieve this result is to have the second garment-facing layer 73 to have a fairly low coefficient of friction. This will allow the anchor 24 to freely move against the undergarment or other clothing worn by the user. If the garment-facing layer does not freely move as desired against the undergarment or other clothing worn by the user, the absorbent article may catch on the undergarment or clothing, which may result in the absorbent article being prematurely and undesirably removed from the user or may cause the absorbent article to be shifted from its desired placement against the body of a user.

In order to achieve the desired coefficient of friction on the garment-facing layer 73 of the anchor 24, the materials used to prepare the shell may be selected such that the garment-facing layer 73 will inherently have the desired coefficient of friction. Alternatively, the garment-facing layer 73 may be treated with a coating composition, such as a polytetrafluoroethylene coating, a silicone containing coating or other similar coating having low coefficient of friction properties. Alternatively, the garment-facing layer 73 could be made from a laminate of two or more materials such that the body-side layer 71 of the anchor 24 is prepared from a material which meets desired properties, while the material selected for the garment-facing layer 73 of the anchor 24 meets the desired coefficient of friction such that the anchor 24 will freely move against the undergarment or garment being worn by a user.

In one embodiment of the present invention, the material used for the pad topsheet 22 may differ from the body-facing layer of anchor 24. It may be desirable to use a more fabric-like material for the layer 73 because the anchor contacts the inner thighs. In one non-limiting example, the topsheet 22 may be a film cover, and the anchor 24 may have a layer 73 of nonwoven, spunlace, or through-air-bonded-carded web. However, any combination of materials may be used for the topsheet 22 and the anchor body-facing layer.

Though desirable in an embodiment where the backsheet 23 is liquid impervious, it may not be necessary to have anchor 24 be liquid impermeable. In such an embodiment, the backsheet 23 functions as a liquid barrier and the anchor 24 need only be liquid resistant. As used herein "liquid resistant" refers to the property of a material which impedes the transport of liquids through and past such material. Conversely, if the backsheet 23 is liquid permeable, then at least the garment-facing layer of anchor 24 is liquid impermeable.

Desirably the anchor 24 is not noisy, to provide discretion for the wearer. The anchor 24 may also be impervious to malodorous gases generated by absorbed bodily discharges, so that the malodors do not escape and become noticed by the wearer. Further, the anchor 24 may be treated with odor-controlling or absorbing materials such as baking soda, activated carbon, zeolites, EDTA, or treated with functional fragrances to mask or control odor.

Anchor 24 may include any desired pattern of embossments formed into at least the body-side layer 71. The embossing can deform at least the body-side surface of the layer 73 to provide operative channel regions that can help block, direct or otherwise control a desired movement of liquids along the bodyside surface of the article. The embossing can also provide an aesthetic benefit to the consumer, and a visual cue regarding fit and leakage protection. The embossments may be configured to provide a regular or irregular pattern having one or more channels which are distributed in a symmetrical or asymmetrical array, as desired.

In a particularly desirable embodiment, the anchor 24 is larger than the pad 21. In such an embodiment, the pad 21 is peripherally circumscribed by the anchor 24, which may have a radial margin of about 0.5 centimeters to about 1.5 centimeters, from the nose end 32 and the tail end 33 of the pad 21. This geometry provides a marginal area of protection should the absorbent body 26 become overloaded, or the pad 21 otherwise fail.

Figure 14A:
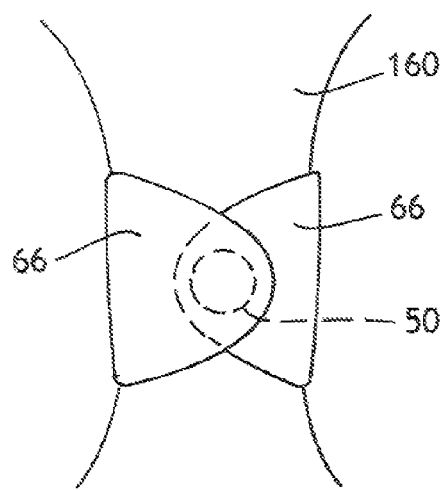
FIG. 14A is a bottom view of another embodiment of the absorbent article showing only the wings fastened to each other so that the absorbent article has a sliding relationship with respect to the undergarment.

Most desirably, the anchor 24 includes a system of wing portions or wings 66 extending outwardly from each longitudinal edge 68 of the anchor 24. As representatively shown in FIGS. 1 and 3, a laterally opposed pair of wings portions can be operatively connected to appointed sections of the longitudinal edges 68 along the intermediate portion 77 of the article 20. In another embodiment (not shown), each wing 66 can be asymmetric along the longitudinal direction Y. Accordingly, the contour shape at one longitudinal end-section of an individual wing may differ from the contour shape at the second longitudinal end-section of the wing. The asymmetric shape of the wings can help improve their ability to maintain the desired positioning of the article in the wearer's undergarment while providing desired levels of comfort and fit against the wearer's body. Asymmetrical wings 66 can be particularly useful when the article 20 is configured to accommodate thong-type undergarments. In another embodiment, the wings 66 may decrease in length along the y-direction so as to have a V-shape or the like, as seen in FIG. 14A. The wings 66 may be fastened to one another or to the undergarment 160 by a fastener having a relatively small area, such as an adhesive 50, hook and loop, microprotusions, snaps, clasps, or other mechanical fasteners. The employed wings 66 can, for example, be separately provided members (not shown) that are subsequently attached or otherwise operatively joined to the intermediate portion of the article 20. In the most desired configurations, the wings are unitarily formed with one or more components of the article. As representatively shown in FIG. 1, for example, both wing portions may be formed from a corresponding, operative extension of the material or materials employed to form the remaining portions of anchor 24.

Referring to FIG. 2, if desired, the outwardly oriented surface 48 of the anchor garment-facing layer may comprise one or more fasteners for affixing the absorbent article 20 to the undergarment of the wearer or to itself to form a wrap about an undergarment crotch region (not shown). Preferred fasteners 48 include mechanical fasteners or, more desirably, pressure sensitive adhesive 50. For example, a pressure sensitive adhesive 50 may be applied to the outwardly oriented surface 48 in two parallel lines or two symmetrically opposite lines. The lines may be about 5 to about 20 millimeters in width. Alternatively, the adhesive 50 may be applied to the anchor 24 in a generally centered rectangular patch (not shown) covering about 30 to about 70 percent of the area of the surface 48. Another alternative, as illustrated, is adhesive 50 longitudinally centered and disposed near the distal end of each wing 66. In addition to or instead of an adhesive 50, the fasteners 48 may be hook and loop, cohesive, or a series of microprotrusions. In addition to the adhesive 50 on the wings, an adhesive may be placed on the garment-facing surface of anchor 24, in particular, along the longitudinal axis as is known in art. However, it is not necessary to adhere the anchor 24 directly to the wearer's undergarment.

Suitable materials from which the garment-side layer 73 may be constructed include bicomponent films or other multicomponent films. In addition, woven and/or nonwoven fabrics which have been treated to render them operatively liquid-impermeable may also be used. Another suitable material can include a closed-cell polyolefin foam, a polyurethane polymer material, a silicone polymer or other similar materials. Silicone polymers having naturally occurring adhesive properties or silicone polymers having a silicone adhesive layer applied thereto may be of particular interest for the layer 73 material.

If desired, the anchor 24 may have notches or slits 107 located at or near the junction of side 68 and wing 66. This may serve to prevent bunching of the undergarment.

The tether system 70 serves to permanently join the anchor 24 to the pad 21 while allowing the anchor 24 and pad 21 to decouple, or in some embodiments of the present invention, partially decouple.

In one embodiment of the present invention, the tether system 70 may include one or more flaccid connectors 72. The flaccid connectors 72 may have various sizes and configurations, as described below. When only a single flaccid connector 72 is present, it may be configured to function as a pivotal connector.

Referring now to the absorbent article embodiment shown in FIG. 2, a pair of flaccid connectors 72 is used to connect pad 21 to anchor 24. Each flaccid connecter 72 has a Z-fold configuration. However, as may be seen in FIG. 4, flaccid connectors may have not only a Z-fold (FIG. 4a), but a C-fold, (FIG. 4b) or a flexible barbell (FIG. 4c) configuration as well. Other fold configurations are possible, including controlled or random pleats or folds. Each flaccid connector 72 configuration may have an advantage over another with respect to manufacturability, cost, and possibly function. For example, the barbell configuration provides the least restraint of motion in the X-, Y-, and Z-directions, and may provide the best way to achieve a pivotal motion of the pad 21 with respect to anchor 24.

Figure 4:
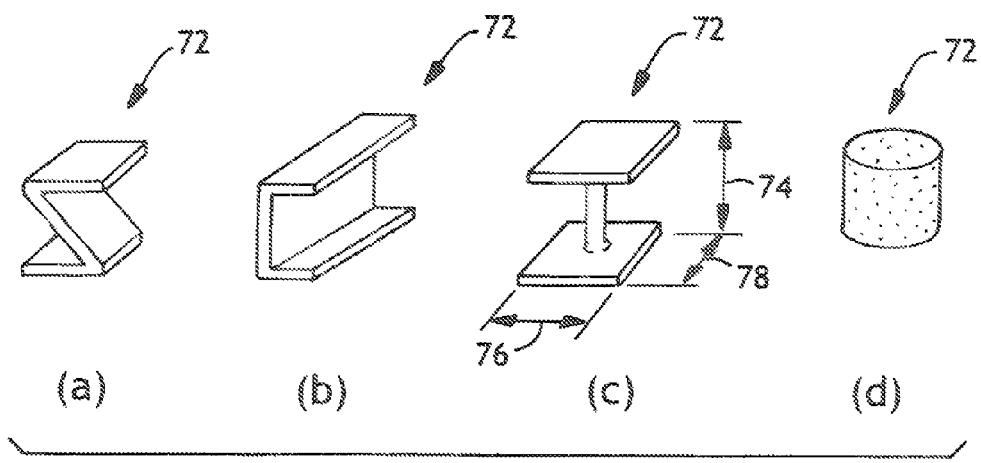
FIG. 4 shows three side perspective views (a-c) of different embodiments of the flaccid connector of the present invention.
Figure 5:
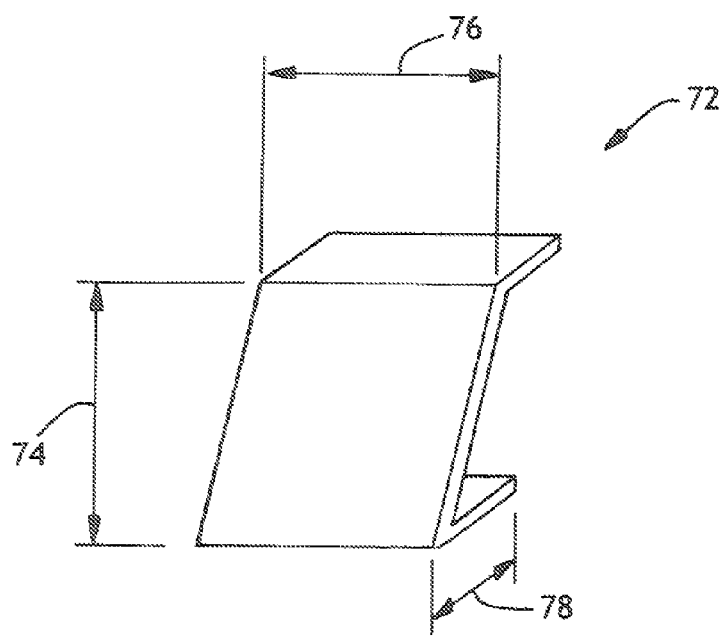
FIG. 5 is a rear perspective view of the flaccid connector shown in FIG. 4(*c*)

Referring now to FIGS. 4(a, b) and 5, the Z-fold and C-fold connectors 72 may have different desired dimensions depending on the desired movement between pad 21 and anchor 24. The connector 72 shown in FIG. 5 has a height 74, a width 76, and a depth 78. The height 74 controls how far the pad 21 can decouple from anchor 24 where the connector 72 is connected. The width 76 controls how far the pad 21 can translate with respect to anchor 24 when each such component is in a parallel plane. The depth 78 has no bearing on motion between the pad 21 and anchor 24, but only serves to define the area of attachment (along with width 76) between the anchor and pad, and connector 72. Referring to barbell connector of FIG. 4(c), the depth 78 and width 76 has no bearing on motion between the pad 21 and anchor 24, but serves to define the area of attachment between these components and the connector 72. However, the height 74 controls how far the pad 21 can decouple from anchor 24 where the connector 72 is connected.

The desired height 74, and possibly the width 76, may be determined by the number and style of connectors 72 used, and the placement of each connector between the anchor 24 and pad 21. Shown in FIG. 3 is one embodiment of a relatively simple article 20 configuration wherein a connector 72 is placed at the target 80, between the pad 21 and the anchor 24. Because only one connector 72 is used, the pad 21 may pivot with respect to anchor 24. Pad 21 may pivot at an angle 82 with respect to the longitudinal axis 84, in either direction therefrom. In one embodiment, the angle 82 is about 40 degrees or less. In another embodiment the, the angle 82 is 35 degrees or less. In yet another embodiment, the angle is 25 degrees or less. Desirably, angle 82 is no less than about 10 degrees. The barbell-style connector 72 will most easily accommodate any angle the pad 21 would like to twist, even allowing perhaps a full 360 degree turn. However, as it may not be necessary to rotate beyond 40 degrees, the Z-shape and C-shape connectors may work as effectively, depending on their height 74 and width 76. Desirably, the height 74 for any of the connectors 72 ranges from about 1 to about 100 mm, this measurement includes the possibility that connecter 72 is elastic or extensible. In another embodiment, the height ranges from about 1 mm to about 40 mm. Most desirably, the height 74 is about 2 mm to about 30 mm. The greater the height 74, the greater the width 76 can be and still provide the desired range of rotation.

Flaccid connectors 72 of FIG. 4(a-b) may be made from the same sheet materials from which the backsheet 23 is constructed. For example, flaccid connectors 72 in the form of a sheet member may be made from a polymeric film, a woven fabric, a nonwoven fabric or the like, as well as combinations or composites thereof. For example, the flaccid connector 72 may include a polymer film laminated to a woven or non-woven fabric. In a particular feature, the polymer film can be composed of polyethylene, polypropylene, polyester or the like, as well as combinations thereof. The thickness, density, and basis weight of the flaccid connectors are chosen to withstand highest stresses the article 20 will endure, which is brought on by a user pulling down the undergarments to which the article 20 is attached. Flaccid connector 4(c) may be made from an injection molded polymer or other moldable materials. Further, the connectors 4(a-c) may be extensible or elastic.

In yet another embodiment of the present invention, the tether system 70 may be in whole or in part made with non-flaccid connectors 172. Non-flaccid connectors 172 may be a layer of adhesive, hook and loop, foams, or direct connections such as that made by pressure bonding, thermal bonding, or the like. Generally, the non-flaccid connectors measure 1-10 mm in the Z-direction. (See, for example, the non-flaccid connector of FIG. 4(d), defined by a foam column.)

Figure 15:
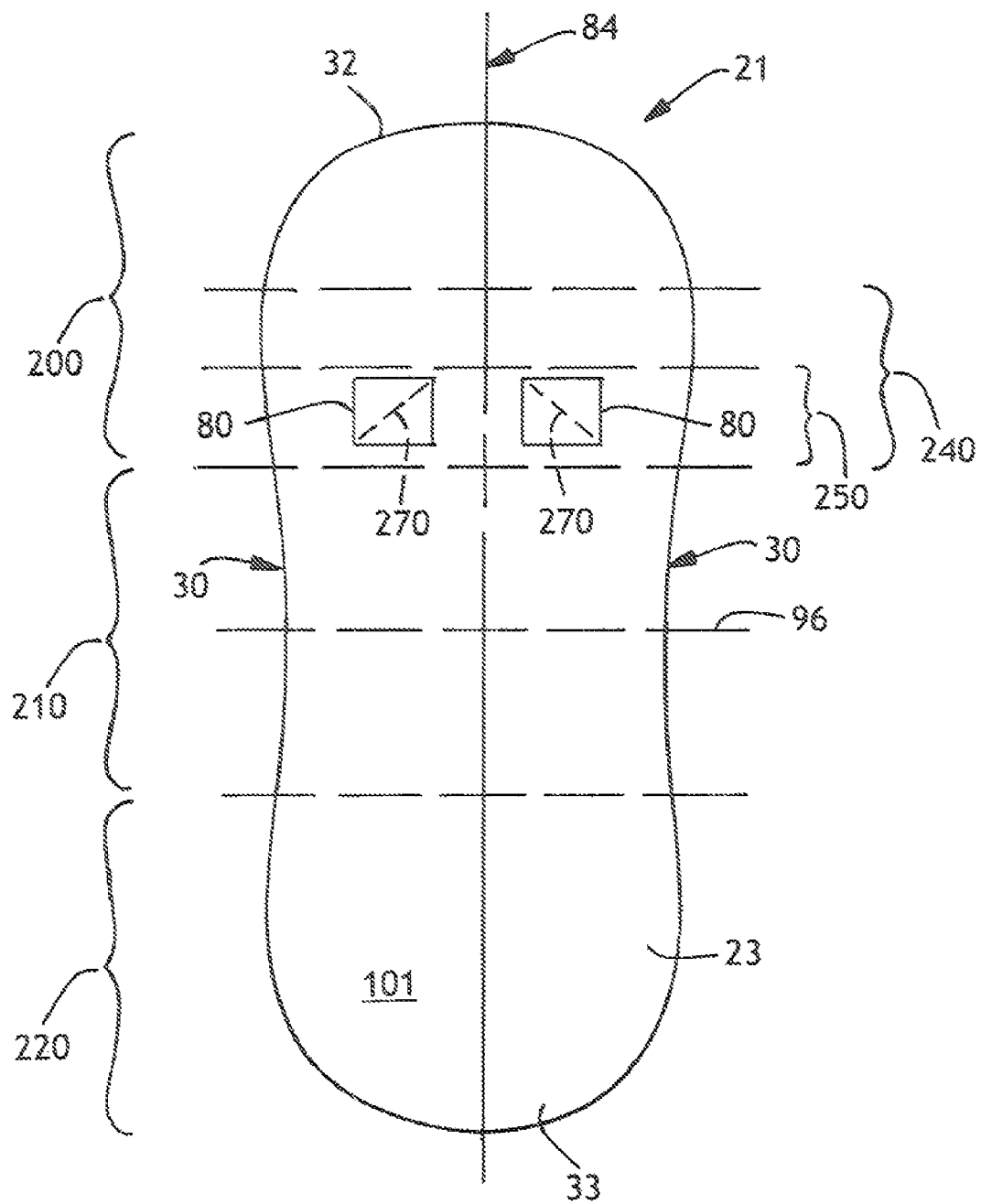
FIG. 15 is a bottom plan view of an absorbent pad of the present invention, showing regions where connectors may be attached to the pad, which may be used with the various embodiments of the present invention, the pad divided into portions and showing one possible target placement.

In one particular embodiment, the non-flaccid connector is made from a layer of construction adhesive. Desirably, the adhesive is roughly applied as circular or square patch. The adhesive patch may have a lateral width that is less than about one-half of the lateral width of the pad 21 where the adhesive is applied. For example, if the lateral width of the pad 21 where the adhesive is applied is about 5 cm, the lateral width of the adhesive patch is 2.5 cm or less, with a practical minimum width of about 5 mm. In another embodiment, the lateral width of the adhesive patch is less than about one-third of the lateral width of the pad 21 where the adhesive is applied. One distinct advantage of having the adhesive patch be narrower than the pad 21 is to allow the side edges 30 of pad 21 to rise away from anchor 24, and seat against the wearer's body when the pad 21 is in use. If the adhesive patch is placed away from the nose end 32 of pad 21 by at least 1 cm, then the nose edge 32 may rise away from the anchor 24 along with the edges 30 to create a "cupping" effect in the anterior portion 200 of pad 21. (The absorbent pad is equally divided along the longitudinal axis 84 into the anterior portion 200, a middle portion 210, and a posterior portion 220 as shown in FIG. 15). Desirably, non-flaccid connectors 172 are located only in the anterior portion 200 of pad 21, and in particular, the middle zone 92. This allows disengagement of the regions surrounding the non-flaccid connector.

A permanent attachment between the flaccid connectors and certain non-flaccid connectors and the pad 21/anchor 24 may be achieved with construction adhesives. Examples of useable construction adhesives include any adhesive which will effectively hold the tether system components in place, so as not to be separated from the pad 21 or the anchor 24. Commercially available construction adhesives usable in the present invention include, for example include Rextac adhesives available from Huntsman Polymers of Houston, Tex., as well as adhesives available from Bostik Findley, Inc, of Wauwatosa, Wis. Other methods may be used to hold the tether system components to the pad or anchor including heat and/or pressure bonding and ultrasonic bonding.

Figure 6:
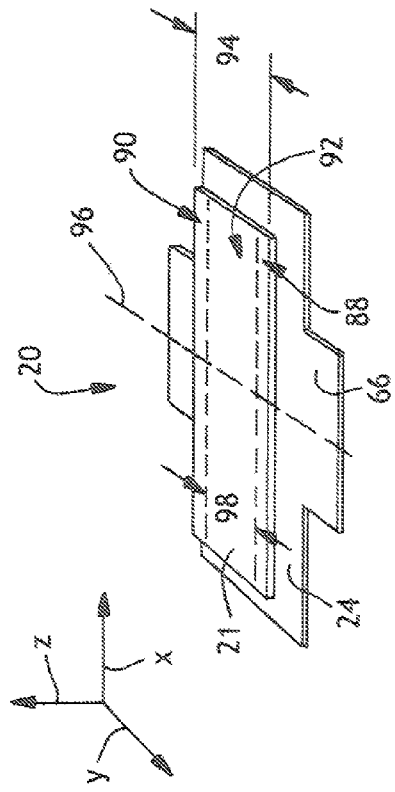
FIG. 6 is a side perspective view of another embodiment of the present invention, in an open condition.

Referring now to FIG. 6, a schematic embodiment is shown in basic rectangular shapes for ease of demonstrating the location of zones on a pad 21. The concept of zones may be applied to any pad configuration, such as that shown in FIG. 1. Each pad 21 may be divided into three laterally disposed areas, a first side zone 88, a second side zone 90, and a middle zone 92 located therebetween. Desirably, the sum width of the threes zones 88, 90, and 92 added together is equal to the width 94 of pad 21, as measured at the lateral axis 96.

The middle zone 92 describes the zone where one or more tether system 70 components are attached to the underside surface 101 of pad 21 (see FIG. 2). Tether system 70 is not located within either side zone 88 or 90. Desirably, the middle zone 92 is oriented symmetrically about the X-direction longitudinal axis. The middle zone 92 may cover from 5 percent to 95 percent of the surface area defined by the pad body-facing surface 98. In another embodiment, the middle zone 92 may cover from 15 percent to 85 percent of the surface area defined by the pad body-facing surface 98. In yet another embodiment, the middle zone 92 may cover from 25 percent to 60 percent of the surface area defined by the pad body-facing surface 98.

Figure 8:
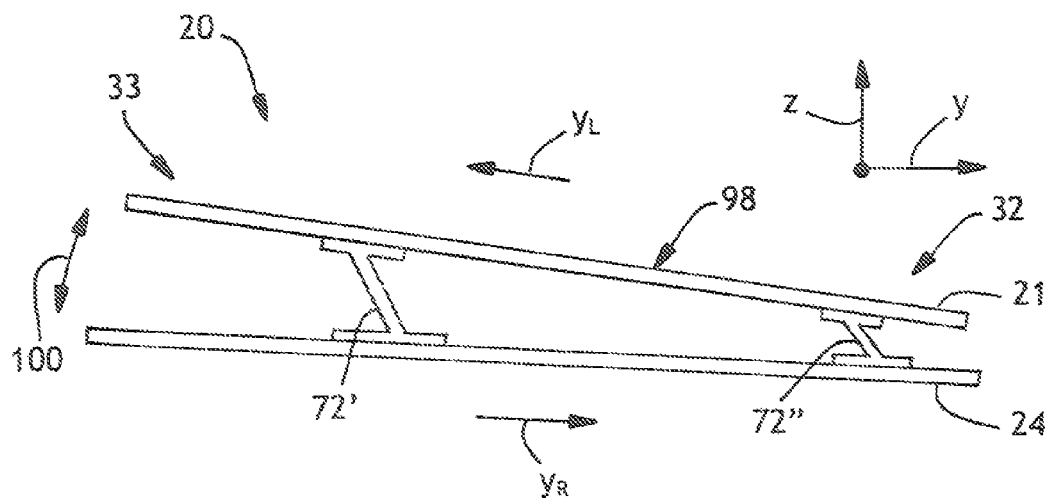
FIG. 8 is a schematic side elevation of the pad and anchor components of the present invention, in a decoupled and translated position.
Figure 9:
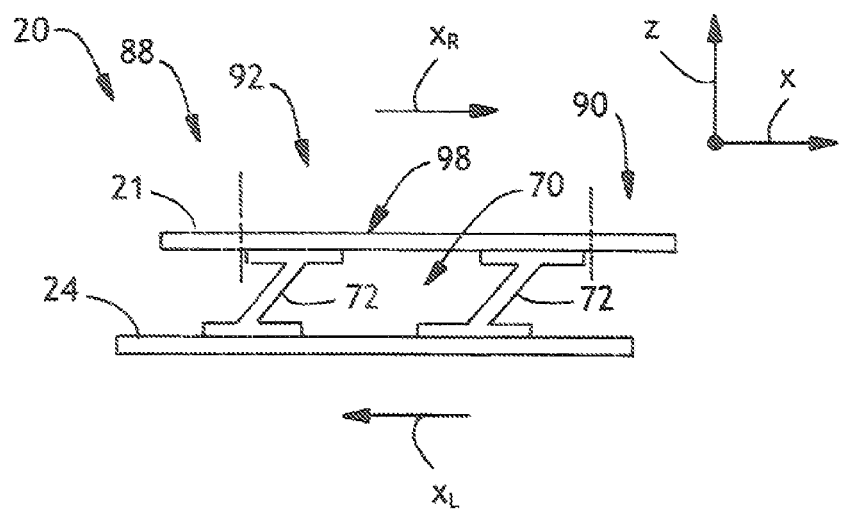
FIG. 9 is a schematic rear elevation of the pad and anchor components of the present invention, in a decoupled and translated position.

Referring now to FIGS. 8 and 9, one embodiment of the absorbent article 20 according to the present invention articulates between closed and open positions. FIGS. 8 and 9 are shown in simple schematic forms for ease of understanding and illustration. However, it should be understood that the pad 21 may have a peaked profile as seen in FIG. 2A. In the "closed position" (not shown), the underside surface 101 of pad 21 makes substantial direct contact with the body-side surface 73 of anchor 24. In the open or "decoupled position" as shown in FIGS. 8 and 9, the pad 21 and anchor 24 are completely separated in the Z-direction, relative to each other, from their respective closed positions.

Figure 7:
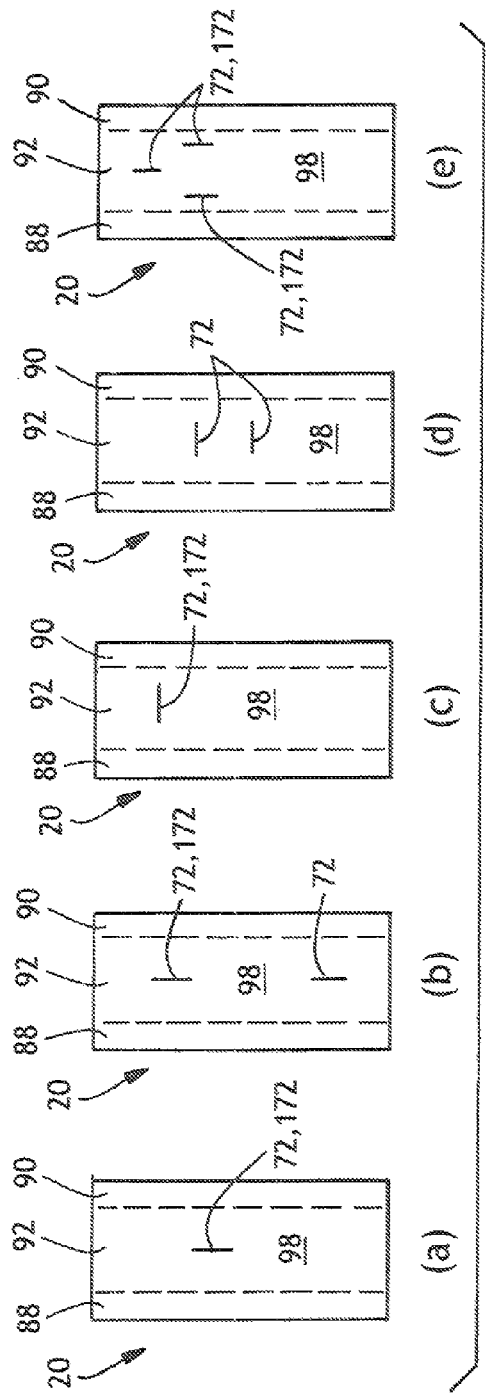
FIG. 7 shows four schematic views (a-e) of the pad shown in FIG. 6, each plan view indicating the intended position or more connectors in various positions between the pad and the anchor.

Referring now to FIG. 7, there are several non-limiting examples of locations and possible orientations of the flaccid connector(s) 72 between pad 21 and anchor 24. In FIG. 7(a), there is a single flaccid connector 72(a or b) having its width 76 (see FIG. 5) substantially aligned with and corresponding to the longitudinal axis of pad 21. In FIG. 7(b), there is a pair of flaccid connectors 72(a or b) spaced apart longitudinally, and each having its width 76 substantially aligned with and corresponding to the longitudinal axis of pad 21. In FIG. 7(c), there is a single flaccid connector 72(a or b) having its width 76 substantially parallel with the lateral axis of pad 21. In FIG. 7(b), there is a pair of flaccid connectors 72(a or b) spaced apart longitudinally, and each having its width 76 substantially parallel with the lateral axis of pad 21. In any of the embodiments shown in FIG. 7, a flaccid connector 72(c) may be substituted for any of the flaccid connector 72(a, b). Further, a non-flaccid connector may be substituted for any connector located in the anterior portion 200 of pad 21.

Depending on the type, number, and orientation of each flaccid connector 72, the separation, translation, and rotation of pad 21 with respect to anchor 24 may be controlled. Comparatively speaking, a single flaccid connector 72 (e.g. FIGS. 7(a or c) will allow more rotation than a pair of identical tether members spaced apart on pad 21 (e.g. FIGS. 7(b or d), especially if they are spaced relatively far from each other. Further, tether members having a relatively shorter height 74 will translate in the X- or Y-plane less than a taller height. Relatively short flaccid connector 72(and b) will rotate less than a similar taller flaccid connector. There is little difference in the height/rotation relationship of flaccid connector 72(c).

The maximum amount of distance and translational movement between the pad 21 and anchor 24 is controlled by the flaccid connectors 72. For instance, as shown in FIG. 8, there is a flaccid connector 72' located near the tail end 33 of the pad 21, and a flaccid connector 72" located near the nose end of pad 21. (Flaccid connector 72" is illustrated as a 72(c)-type tether, but could be a 72(a or b)-type tether.) If the pad 21 and anchor 24 translate in opposite Y-directions, namely, respective directions $Y_L$ and $Y_R$, then the tail portion 33 of pad 21 will move rearward on anchor 24. As the flaccid connector 72" is shorter than the flaccid connector 72', the pad 21 may form angle 100 with anchor 24, such that the tail portion 33 raises closer to the body of the wearer than the nose portion 32.

Referring now to FIG. 9, there is another example of how the maximum amount of distance and translational movement between the pad 21 and anchor 24 is controlled by the flaccid connector 72. For instance, a flaccid connector 72 is symmetrically placed within the middle zone 92, desirably in the intermediate portion 77 of absorbent article 20. If the pad 21 and anchor 24 translate in opposite X-directions, namely, respective directions $X_R$ and $X_L$, then the pad 21 translates to the right with respect to anchor 24.

Figure 10:
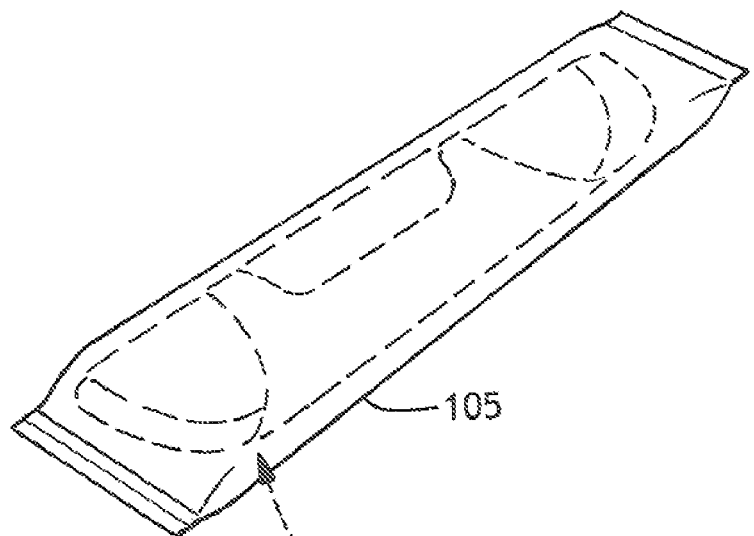
FIG. 10 is a top perspective view of the absorbent article of FIG. 1, showing one embodiment of how the absorbent article may be folded and wrapped in a package.

Referring now to FIG. 10, article 20 may be folded and packaged in an individual packet 105. Most desirably, the article 20 is folded along its longitudinal axis so that the topsheet 22 faces outward. This can serve to pre-shape the pad 21 into a body-contacting shape for wearer. It is further contemplated that the article 20 could be packaged without folding or wrapping, or folded into a dual- or tri-fold as is known in the art.

Figure 13:
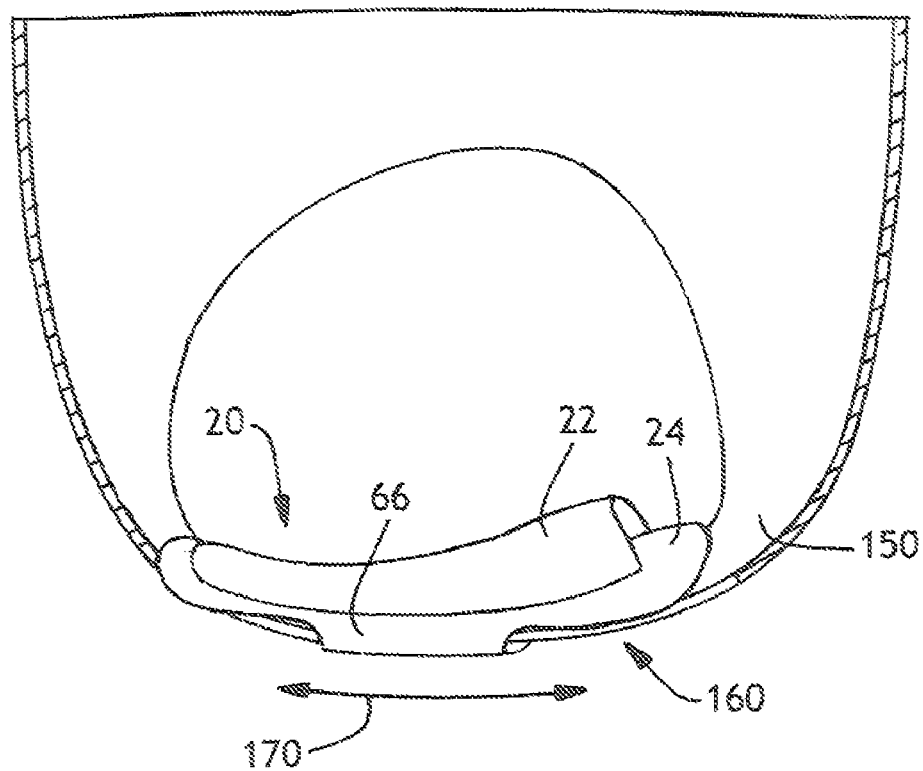
FIG. 13 is a side view of the absorbent article of FIG. 1, fastened onto an undergarment shown in a cut-away view.

In another embodiment of the present invention, pad 21 may be flat or may have a three-dimensional shape prior to packaging. By preforming the pad 21 with a three-dimensional saddle-like shape as is shown in FIG. 13, placement of the article may be easier for the user. Generally, the three-dimensional shape could be such that it closely matches the overall general curvature of the vulva region and optionally the pubic and perinea regions of most women, when the absorbent article is used as a pantiliner, sanitary napkin or a feminine incontinence article. To form the pad 21 with a three-dimensional shape, the pad may be molded in any manner known to those skilled in the art, for example heat molding. The manner in which the three-dimensional shape is imparted to the shell 14 is not critical to the present invention.

Figure 11:
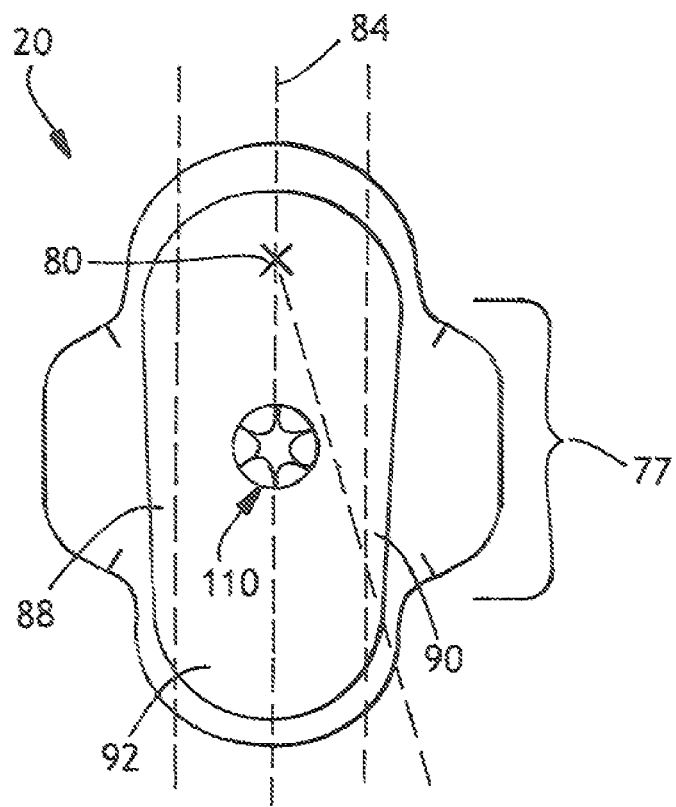
FIG. 11 is a plan view of another embodiment of the absorbent article of the present invention having an aperture for receiving bodily fluid as menses.

Referring now to FIGS. 11 and 12, shown is a second embodiment of the present invention. This embodiment is identical to the first embodiment and all of its potential variations with the exception that (1) it includes a portal 200 through the topsheet 22 and a portion of the absorbent body 26, and (2) it has liquid impermeable members inserted within the absorbent body as described below.

FIG. 12 shows the most desired relationship between the various layers of pad 21'. Of course, other configurations are possible. The pad 21' has a topsheet 22 with portal defined by edge 110. Directly underneath the topsheet 22 is a surge layer 81. Desirably surge layer 81 includes slits 93 to assist with pad shaping. Surge layer 81 also includes a portal that is aligned with that in the topsheet. The portal is defined by an edge 112. Directly underneath the surge layer is a meltblown layer 83. Meltblown layer may include a portal similar to that of the surge layer, or may have a portal defined by an edge with petals 114 around the circumference of the portal. The petals add a softer look to the portal. Directly underneath the meltblown layer 83 is a hydrophobic member 116. Desirably, the surface area of the hydrophobic member is less than that of the other preceding layers. The hydrophobic member is made from a liquid impermeable polymer sheet. Menses in particular will flow along the hydrophobic member to the shaping layer 85 located directly below. Shaping layer 85 may include slits 93 or scores as described previously. A backsheet 23 is the final layer. The pad 21' may be attached to the anchor 24 in the many ways demonstrated earlier. In the embodiment shown in FIG. 12, the pad 21 is attached to anchor 24 with a layer of adhesive 50.

In operation, a wearer of any embodiment of the absorbent article 20 may use the product as follows. The wearer removes the article 20 from the packaging and spreads it out to ready it for use. The wearer aligns the pad 21 with the desired body orifice (e.g. vaginal opening) to maximize the absorption of bodily exudates. Instructions may be provided with the article 20 that instruct the user to align the pad 21 with the body orifice at issue. If there is a portal 200 present on the absorbent article, the pad 21 is aligned with so that liquids emitted from the body orifice will be directed at the portal 200. The anchor member 24 is fastened to the wearer's undergarment. The act of fastening the anchor member 24 to the undergarment desirably takes place after the wearer aligns the pad 21 with the desired orifice, though some wearer may prefer to first fasten the anchor 24 to the wearers undergarment.

Figure 14:
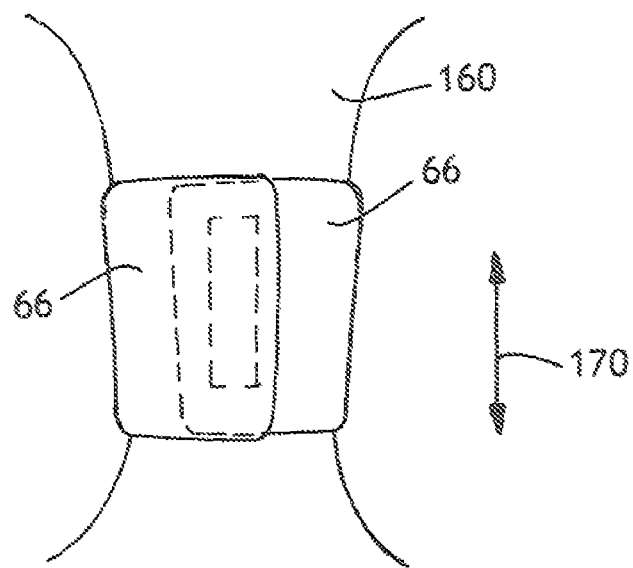
FIG. 14 is a bottom view of the absorbent article of FIG. 13, showing the wings fastened to each other so that the absorbent article has a sliding relationship with respect to the undergarment.

In an alternative embodiment as shown in FIGS. 13 and 14, the wings 66 may be wrapped about the crotch portion 160 of the wearer's undergarment 150 and joined together without adhering to the undergarment. This way, the anchor 24 may have a sliding association with the undergarment, allowing for adjustment of pad position. The sliding direction 170 of article 20 is generally parallel to the longitudinal direction of pad 21.

In a further embodiment shown in FIG. 15, an absorbent pad 21 a desired location for two targets 80 is shown. As described previously, target 80 is where a connector 72 may be attached at the underside surface 101 of the absorbent pad 21. The absorbent pad is divided into the anterior portion 200, a middle portion 210, and a posterior portion 220. The anterior portion 200 is further halved longitudinally to form an interior region 240 directly adjacent the middle portion 210. The interior region 240 is further halved to form a sub-interior region 250. Desirably, the targets 80 are located in the interior region 240. Even more desirably, the targets 80 are located in the sub-interior region 250. The targets 80 may be two in number, and symmetrically spaced apart from one another with respect to the longitudinal axis 84. If the connector 72 (not shown) is a film member, then it may be oriented diagonally across the target 80 area, as shown by phantom lines 270.

Although the present invention has been described with reference to various embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

The invention claimed is:

1. A method of maintaining contact between an absorbent pad having a body-facing surface, and a perineal-region orifice of the human body, the method comprising the steps of:
providing an absorbent pad comprising,
a liquid-permeable topsheet adapted to be oriented towards and in contact with the body of a wearer,
a liquid-impermeable back sheet oriented away from the body of the wearer, and
an absorbent body located between the topsheet and the back sheet, the absorbent body comprising,
a surge layer, a meltblown layer, and an absorbent layer wherein the topsheet includes a portal, the surge layer includes a portal aligned with the portal in the topsheet, and the meltblown layer includes a portal aligned with the portal in the topsheet;
providing a flexible and liquid-impermeable anchor member adapted to be oriented towards and in contact with an undergarment of the wearer,
connecting the absorbent pad to the anchor member by at least two connectors that allow the absorbent pad to move in a longitudinal, lateral, and vertical direction with respect to the anchor member;

folding the absorbent pad along a longitudinal axis such that the bodyfacing surface faces outward, and maintaining a folded configuration in a package prior to use; and providing instructions to align the absorbent pad with the perineal-region.

2. The method of claim 1 wherein the at least two connectors are flaccid connectors.

3. The method of claim 1 wherein the topsheet is treated with a surfactant or menses modifier.

4. The method of claim 1 wherein the anchor is adapted to fasten to the underwear of the wearer in a sliding association.

5. The method of claim 1 wherein the step of providing the absorbent pad includes the step of positioning the surge layer immediately underneath and in contact with the topsheet.

6. The method of claim 5 wherein the step of providing the absorbent pad includes the step of positioning the meltblown layer directly underneath and in contact with the surge layer.

7. The method of claim 6 wherein the step of providing the absorbent pad includes the step of positioning the absorbent layer directly underneath the meltblown layer.

8. The method of claim 1 wherein the anchor member includes a body-facing layer and a garment-facing layer.

9. The method of claim 8 wherein the step of providing the anchor member includes the step of treating the garment-facing layer with a coating composition having low coefficient of friction properties.

10. The method of claim 1 wherein the at least two connectors have a flexible barbell configuration.

11. The method of claim 1 wherein the portal of the meltblown layer defines an edge with petals around the circumference of the portal.

12. The method of claim 1 wherein the absorbent pad further includes a hydrophobic member positioned directly underneath the meltblown layer and above the absorbent layer.

13. A method of maintaining contact between an absorbent pad having a body-facing surface, and a perineal-region orifice of the human body, the method comprising the steps of:

providing an absorbent pad comprising,
　a liquid-permeable topsheet adapted to be oriented towards and in contact with the body of a wearer,
　a liquid-impermeable back sheet oriented away from the body of the wearer, and
　an absorbent body located between the topsheet and the back sheet, the absorbent body comprising,
　　a surge layer, a meltblown layer, a hydrophobic member, and an absorbent layer, wherein the topsheet includes a portal, the surge layer includes a portal aligned with the portal in the topsheet, and the meltblown layer includes a portal aligned with the portal in the topsheet, wherein the portal of the meltblown layer defines an edge with petals, and wherein the surge layer is positioned immediately underneath and in contact with the topsheet, the meltblown layer is positioned directly underneath and in contact with the surge layer, the hydrophobic member is positioned directly underneath the meltblown layer and above the absorbent layer;

providing a flexible and liquid-impermeable anchor member adapted to be oriented towards and in contact with an undergarment of the wearer, connecting the absorbent pad to the anchor member by at least one connector that allows the absorbent pad to move in a longitudinal, lateral, and vertical direction with respect to the anchor member; and folding the absorbent pad along a longitudinal axis such that the body-facing surface faces outward, and maintaining a folded configuration in a package prior to use.

* * * * *